(12) United States Patent
Zentgraf

(10) Patent No.: US 8,405,519 B2
(45) Date of Patent: Mar. 26, 2013

(54) PULSE EMISSION DEVICE FOR THE POSITIONALLY ACCURATE EMISSION OF TRIGGER PULSES

(75) Inventor: Eberhard Zentgraf, Erlangen (DE)

(73) Assignee: Siemens Aktiengesellschaft, München (DE)

( * ) Notice: Subject to any disclaimer, the term of this patent is extended or adjusted under 35 U.S.C. 154(b) by 775 days.

(21) Appl. No.: 12/518,942

(22) PCT Filed: Oct. 19, 2007

(86) PCT No.: PCT/EP2007/061199
§ 371 (c)(1),
(2), (4) Date: Jun. 12, 2009

(87) PCT Pub. No.: WO2008/071494
PCT Pub. Date: Jun. 19, 2008

(65) Prior Publication Data
US 2010/0019926 A1 Jan. 28, 2010

(30) Foreign Application Priority Data
Dec. 15, 2006 (DE) .......................... 10 2006 059 381
Jun. 25, 2007 (DE) .......................... 10 2007 029 151

(51) Int. Cl.
*G01V 3/00* (2006.01)
(52) U.S. Cl. ..................... 340/855.4; 327/149; 327/158; 327/161; 327/164

(58) Field of Classification Search .............. 340/825.64
See application file for complete search history.

(56) References Cited

U.S. PATENT DOCUMENTS

| 6,625,498 B1 * | 9/2003 | Kurakake et al. ................. 700/3 |
| 2002/0175771 A1 * | 11/2002 | Cyrusian ......................... 331/25 |
| 2006/0259231 A1 * | 11/2006 | Ichikawa et al. .............. 701/115 |

FOREIGN PATENT DOCUMENTS

| DE | 10349948 B3 | 1/2005 |
| EP | 0588512 A1 | 3/1994 |
| EP | 588512 A1 * | 3/1994 |
| JP | 57212466 A | 12/1982 |
| JP | 1133115 A | 5/1989 |
| JP | 2202607 A | 8/1990 |
| JP | 4340399 A | 11/1992 |
| JP | 2004110359 A | 4/2004 |
| JP | 2006316739 A | 11/2006 |
| WO | WO 2005065884 A2 | 7/2005 |

* cited by examiner

*Primary Examiner* — George Bugg
*Assistant Examiner* — Anthony D Afrifa-Kyei
(74) *Attorney, Agent, or Firm* — Henry M Feiereisen LLC

(57) ABSTRACT

A control device (1) and a triggering device (2) are coupled to one another for data processing. The control device and the triggering device (2) are electronic devices. The control device (1) determines a respective desired position value (p*) for at least one shaft with an interpolation cycle (T) and transmits a time delay (t) to the triggering device (2). The triggering device (2) monitors when the time delay (t) expires from transmission of the time delay (t) and then outputs a trigger pulse (I).

13 Claims, 4 Drawing Sheets

PULSE EMISSION DEVICE FOR THE POSITIONALLY ACCURATE EMISSION OF TRIGGER PULSES

CROSS-REFERENCES TO RELATED APPLICATIONS

This application is the U.S. National Stage of International Application No. PCT/EP2007/061199, filed Oct. 19, 2007, which designated the United States and has been published as International Publication No. WO 2008/071494 and which claims the priorities of German Patent Applications, Serial Nos. 10 2006 059 381.2, filed Dec. 15, 2006, and 10 2007 029 151.7, filed Jun. 25, 2007, pursuant to 35 U.S.C. 119(a)-(d).

BACKGROUND OF THE INVENTION

The present invention relates to a pulse emission device having a control device and a triggering device which is coupled to the control device for data purposes, the control device and the triggering device being electronic devices and being designed in such a manner that, during operation of the pulse emission device, the control device determines a respective desired position value for at least one axis at an interpolation clock rate, and the triggering device outputs a trigger pulse when a trigger condition occurs.

For some control processes, it may be necessary to emit a respective trigger pulse to an external device at locally equidistant intervals along a traveled path. The external device may be, for example, an ultrasound measuring head which is used to measure a machined workpiece.

In order to provide such trigger pulses, DE 103 49 948 B3 discloses that the control device outputs the desired position values to a motor which is actually present and to which a displacement sensor system is connected. The output signal from the displacement sensor system is supplied to the control device and is evaluated by the control device. In this case, the desired value is determined by the control device in such a manner that it corresponds to the respective distance covered along the path to be traveled (so-called path axis). Another possibility is to replace the motor with electronics which determine the signals to be emitted by the displacement sensor system in a purely arithmetical manner and output said signals.

In both cases, the displacement sensor signals are returned to the control device and are evaluated by the control device. The control device thus ensures that the correct number of displacement sensor signals is emitted either by the motor/sensor unit or by the electronics within an interpolation clock rate. The actual trigger signal is externally generated in a positionally accurate manner by further electronics and the counting of the displacement sensor signals independently of the clock rate of the control device.

SUMMARY OF THE INVENTION

The object of the present invention is to provide a pulse emission device which can be used to emit trigger pulses at exactly the desired times without the need to return the trigger pulses to the control device.

The object is achieved by means of a pulse emission device having a control device and a triggering device which is coupled to the control device for data purposes, the control device and the triggering device being electronic devices and being designed in such a manner that, during operation of the pulse emission device, wherein the control device determines a respective desired position value for at least one axis at an interpolation clock rate and transmits a time delay (t) to the triggering device, and wherein the triggering device monitors when the time delay expires from the transmission of the time delay and then outputs a trigger pulse.

According to the invention, the control device determines a respective desired position value for at least one axis at an interpolation clock rate. The control device likewise transmits a time delay to the triggering device at the interpolation clock rate. The triggering device monitors when the time delay expires from the transmission of the time delay. It then outputs a trigger pulse.

In the procedure according to the invention, the outputting of the trigger pulse is thus decoupled from the control device and thus also from the interpolation clock rate.

It is possible for the control device to transmit a follow time to the triggering device in addition to the time delay. In this case, the triggering device can monitor when the follow time expires from the outputting of the trigger pulse last output and can then output a respective further trigger pulse.

It is possible for the control device to transmit a pulse number to the triggering device in addition to the time delay and the follow time. In this case, the triggering device outputs the further trigger pulses only until the number of further trigger pulses output since the last transmission of the time delay, the follow time and the pulse number corresponds to the transmitted pulse number.

The control device preferably determines the pulse number using the time delay, the follow time and the interpolation clock rate.

The control device preferably determines the follow time using the time derivative of the desired position value determined for the at least one axis and a local desired distance. This makes it possible for the trigger pulses to be output in a locally equidistant manner by the triggering device in a fashion spanning the interpolation clock rate.

The control device preferably determines the time delay using the time of the trigger pulse last output, the time at which the next desired position value is output, the time derivative of the desired position value determined for the at least one axis and a local desired distance. This measure likewise makes it possible for the trigger pulses to be output in a locally equidistant manner by the triggering device in a fashion spanning the interpolation clock rate.

When determining the time delay, the control device preferably takes into account a delay of an actual position value of at least one further axis in comparison with the desired position value of the at least one axis.

In a multiplicity of cases, the control device is in the form of a numerical controller.

The triggering device is preferably clocked at an internal clock rate which is greater than the interpolation clock rate.

BRIEF DESCRIPTION OF THE DRAWINGS

Further advantages and details emerge from the following description of exemplary embodiments in conjunction with the drawings, in which, in a basic illustration.

DETAILED DESCRIPTION OF PREFERRED EMBODIMENTS

Figure 1:
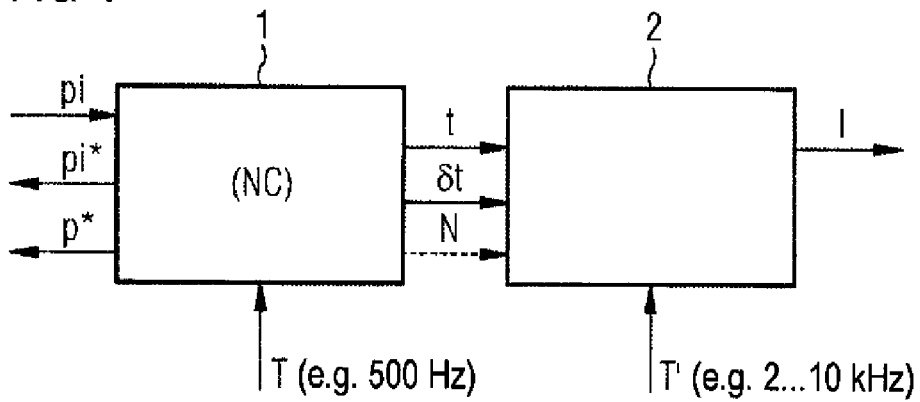
FIG. 1 shows a block diagram of a pulse emission device.

According to FIG. 1, a pulse emission device has a control device 1 and a triggering device 2. The control device 1 and the triggering device 2 are electronic devices. They are coupled to one another for data purposes. The control device 1 may be in the form of a numerical controller, for example. This is indicated by the letters "NC" (=numerical control) in FIG. 1. The triggering device 2 is used to output trigger pulses I.

Figure 5:
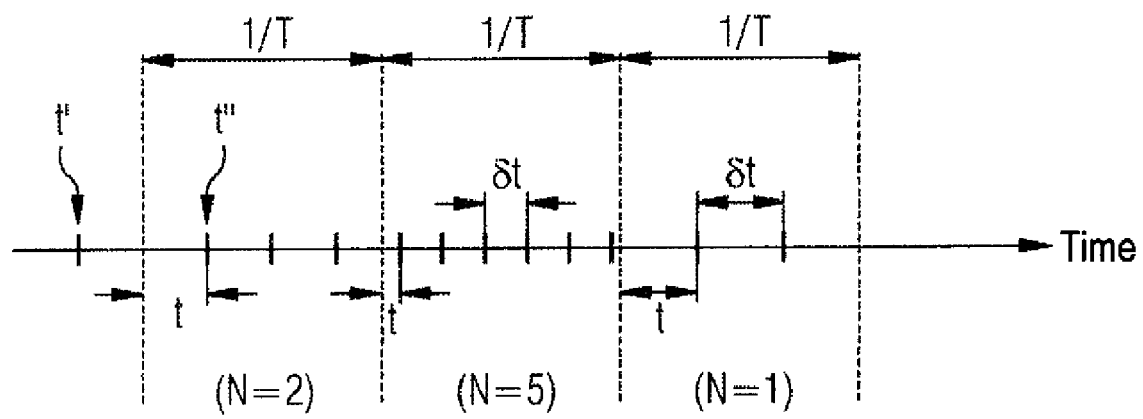
FIG. 5 shows a timing diagram.

The control device 1 is clocked at an interpolation clock rate T. According to the exemplary embodiment (compare FIG. 5), the interpolation clock rate T is 500 Hz. This corresponds to a repetition time of 2 ms. According to the exemplary embodiment, the control device 1 thus determines a desired position value p* for a path axis within every 2 ms. The desired position value p* for the path axis is a value which increases monotonously over time. It corresponds to the total distance covered along a path. In this case, the path is determined by the temporal sequence of all further desired position values pi* which are output to further axes by the control device 1.

Figure 2:
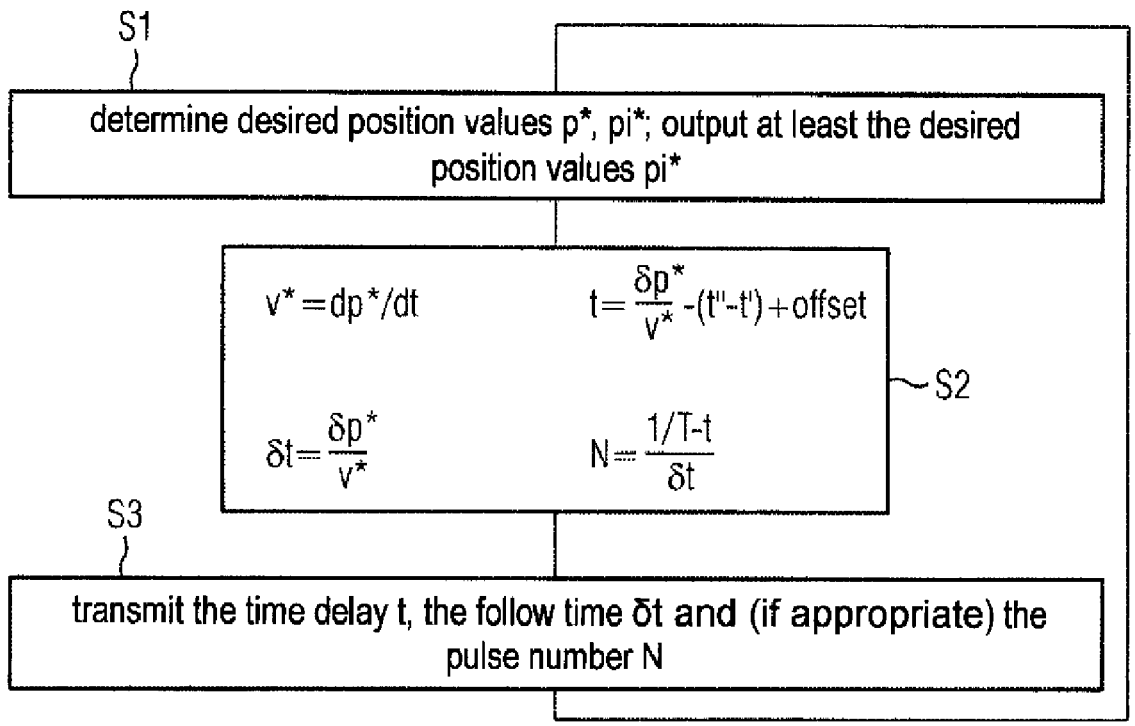
FIGS. 2 to 4 show flowcharts.

According to FIG. 2, the control device 1 determines and, if appropriate, also outputs the desired position values p*, pi* in a step S1. In particular, the further axes are actually set as part of step S1. According to FIG. 2, the control device 1 also carries out steps S2 and S3.

In step S2, the control device 1 determines at least the time derivative v* of the desired position value p* of the path axis. As a result, it thus determines the desired speed v* at which the path of the further axes is traveled along at this time. It also determines a time delay t and a follow time dt. Optionally, it can additionally determine a pulse number N.

The control device 1 determines the time delay t using the time t' of the trigger pulse I last output by the triggering device 2, the time t" at which the next desired position value p* is output, the time derivative v* of the desired position value p* determined for the at least one axis and a local desired distance dp*. In particular, the quotient of the local desired distance dp* and the desired speed v* corresponds to an interval of time which should be present between the next trigger pulse I and the trigger pulse I last output. The trigger pulse last output was output at the time t'. The time delay t thus results as $$t = \frac{dp^*}{v^*} - (t'' - t') + \text{offset}. \quad (1)$$

The offset mentioned in equation 1 may be zero. However, as part of the offset, the control device 1 preferably takes into account a delay of an actual position value pi of at least one of the further axes in comparison with the desired value p* of the path axis. This offset makes it possible to take into account the delay of the actual position values pi in comparison with the corresponding desired position values pi* (that is to say the tracking error). The control device 1 always determines the time delay t in such a manner that the trigger pulses I are output in a locally equidistant manner by the triggering device 2 in a fashion spanning the respective interpolation clock rate T.

The control device 1 also determines the follow time dt using the time derivative v* of the desired position value p* determined for the at least one axis and the local desired distance dp*. In particular, it determines the follow time dt as $$dt = \frac{dp^*}{v^*}. \quad (2)$$

The control device 1 thus also determines the follow time dt in such a manner that the trigger pulses I are output in a locally equidistant manner by the triggering device 2 in a manner spanning the interpolation clock rate.

In the situation in which the control device 1 also determines the pulse number N, the control device 1 determines the pulse number N using the time delay t, the follow time dt and the interpolation clock rate T. In particular, the control device 1 determines the pulse number N, if appropriate, as $$N = \frac{1/T - t}{dt}. \quad (3)$$

In step S3, the control device 1 transmits the time delay t, the follow time dt and, if appropriate, also the pulse number N to the triggering device 2.

Figure 3:
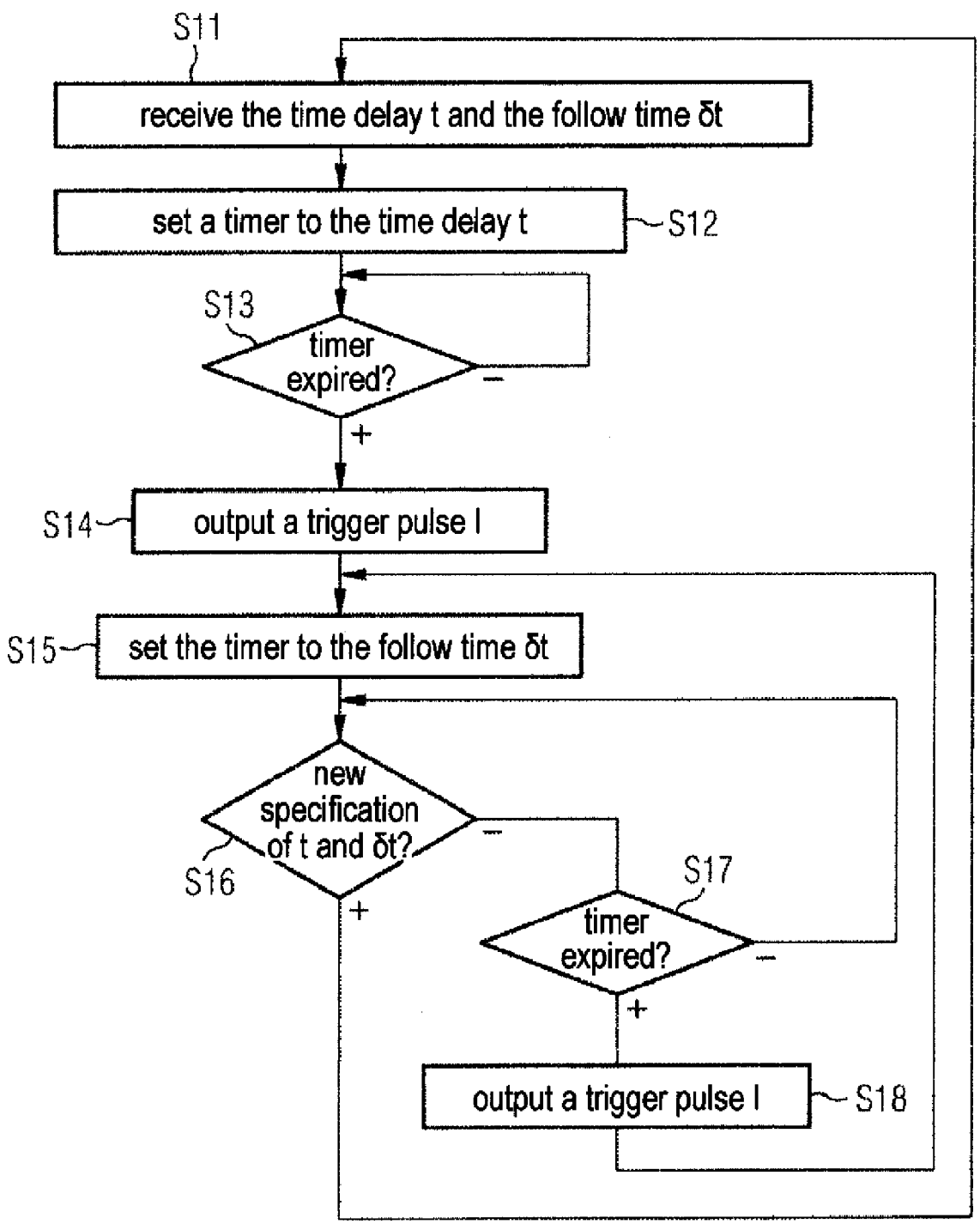
Figure 4:
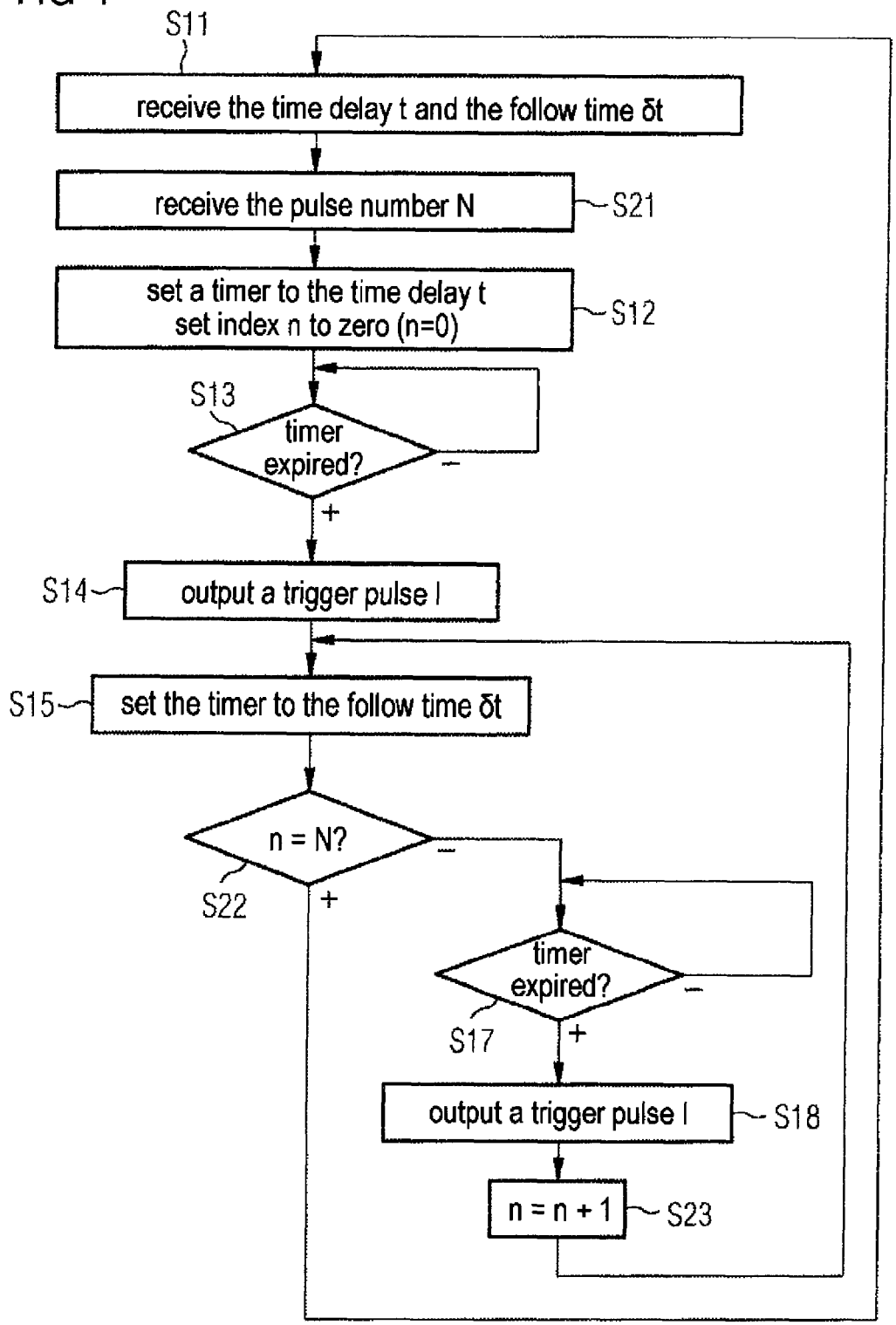

The triggering device 2 is clocked at an internal clock rate T' which is greater than the interpolation clock rate T. For example, the internal clock rate may be 2 kHz, 5 kHz, 10 kHz etc. The triggering device 2 carries out a method according to FIG. 3 or FIG. 4. In this case, FIG. 3 relates to the situation in which the control device 1 transmits only the time delay t and the follow time dt to the triggering device 2. FIG. 4 relates to the situation in which the control device 1 also transmits the pulse number N in addition to the time delay t and the follow time dt. FIG. 3 is discussed first below and then FIG. 4.

According to FIG. 3, the triggering device 2 first of all receives the time delay t and the follow time dt in a step S11. In a step S12, the triggering device 2 sets a timer to the time delay t. In a step S13, the triggering device 2 waits for the expiry of the time delay t. When the time delay t has expired, the triggering device 2 outputs a trigger pulse I in a step S14. The triggering device 2 thus monitors when the time delay t expires from the transmission of the time delay t. It then outputs the trigger pulse I.

In a step S15, the triggering device 2 sets the timer to the follow time dt. In a step S16, the triggering device 2 checks whether the time delay t and the follow time dt are intended to be newly specified. If this is the case, the triggering device 2 returns to step S11. Otherwise, the triggering device 2 carries out a step S17 in which it checks whether the timer has expired. If this is not the case, the triggering device 2 proceeds to step S16. Otherwise, the triggering device 2 carries out a step S18 in which it outputs a further trigger pulse I. From step S18, the triggering device 2 returns to step S15.

The procedure according to FIG. 3 thus results in the triggering device 2 monitoring when the follow time dt expires from the outputting of the trigger pulse I last output and then outputting a respective further trigger pulse I.

The procedure in FIG. 4 is similar to the procedure in FIG. 3. In particular, the procedure in FIG. 4 also comprises steps S11 to S15 and steps S17 and S18 from FIG. 3. However, step S16 is missing. In addition to steps s11 to S15, S17 and S18, there are steps S21 to S23. Only steps S21 to S23 are explained in more detail below.

In step S21, the triggering device 2 receives the pulse number N. It also sets an index n to the value zero. Step S21 may be combined, if appropriate, with step S11 to form a single step.

In step S22, the triggering device 2 checks whether the index n is equal to the pulse number N.

In step S23, the triggering device 2 increments the index n, that is to say increases its value by one.

The procedure according to FIG. 4 results in the triggering device 2 monitoring when the follow time dt expires from the outputting of the respective trigger pulse I last output and then outputting a respective further trigger pulse I. In this respect, the effect of the procedure in FIG. 4 is the same as that in FIG. 3. However, in the refinement according to FIG. 4, the further trigger pulses I are output only until the number of further trigger pulses I output since the last transmission of the time delay t, the follow time dt and the pulse number N corresponds to the transmitted pulse number N.

The procedure according to the invention easily makes it possible for the triggering device 2 to output locally equidistant trigger pulses I. This can be seen in FIG. 5.

The trigger pulses I may be in different forms. In particular, the trigger pulses I may be a simple switching signal. However, displacement sensor signals, for example, could alternatively be simulated.

The procedure according to the invention has many advantages. For example, the trigger frequency may be increased independently of the sampling interval (=reciprocal of the interpolation clock rate T) as long as it is permissible to consider the desired speed v* to be constant within the sampling interval. In addition, hardware can be saved by using electronics. It is also a technically high-quality, future-oriented solution which is very reliable in continuous operation. The procedure according to the invention is also based on calculated desired values which can be determined and reproduced in a very accurate manner. The trigger pulses I may be output with very accurate timing and with a high degree of precision. Jitter effects virtually no longer arise.

The above description is used solely to explain the present invention. However, the scope of protection of the present invention should be determined solely by the accompanying claims.

What is claimed is:

1. A pulse emission device comprising:
an electronic control device operating at an interpolation clock rate, and
an electronic triggering device coupled to the electronic control device for data exchange and operating at an internal clock rate greater than the interpolation clock rate, wherein the electronic control device is configured to
determine at the interpolation clock rate for at least one axis a corresponding desired position value;
determine a time delay corresponding to the desired position value;
transmit the time delay from the control device to the triggering device;
transmits in addition to the time delay a follow-up time determined from a time derivative of the desired position value determined for the at least one axis and a desired local position distance, so that consecutive trigger pulses are outputted by the triggering device with an equidistant local position distance independent of the interpolation clock rate;
wherein the electronic triggering device is configured to monitor an end time of the received time delay
at the end time, output a trigger pulse,
monitor when the follow-up time elapses following output of a last trigger pulse and outputs an additional trigger pulse, wherein the trigger pulse and the additional trigger pulse are outputted independent of the interpolation clock rate of the control device.

2. The pulse emission device of claim 1, wherein during operation of the pulse emission device, the control device transmits in addition to the time delay a follow-up time and a pulse number, and the triggering device monitors when the follow-up time elapses following output of the last trigger pulse and then outputs additional trigger pulses until a number of additional trigger pulses outputted since the most recent transmission of the time delay, of the follow-up time and of the pulse numbers corresponds to the transmitted pulse number.

3. The pulse emission device of claim 2, wherein the control device is configured to determine the pulse number from the time delay, the follow-up time and the interpolation clock rate.

4. The pulse emission device of claim 1, wherein the control device determines the time delay based on a time when the last trigger pulse was outputted, a time when a subsequent desired position value is outputted, a time derivative of the desired position value determined for the at least one axis and a desired local position distance, and wherein the triggering device outputs the trigger pulses with an equidistant local position distance independent of the interpolation clock rate.

5. The pulse emission device of claim 4, wherein the control device takes into consideration, when determining the time delay, a delay of an actual position value of at least one additional axis with respect to the desired position value of the at least one axis.

6. The pulse emission device of claim 1, wherein the control device is implemented as a numerical controller.

7. The pulse emission device of claim 1, wherein the internal clock rate is greater than the interpolation clock rate.

8. A method for emitting accurately timed trigger pulses, comprising the steps of:
determining with an electronic control device operating at an interpolation clock rate a desired position value for at least one axis;
transmitting a time delay corresponding to the desired position value from the electronic control device to an electronic triggering device that operates at an internal clock rate greater than the interpolation clock rate;
during operation of the pulse emission device, transmitting from the control device in addition to the time delay a follow-up time determined from a time derivative of the desired position value determined for the at least one axis and a desired local position distance, so that consecutive trigger pulses are outputted by the triggering device with an equidistant local position distance independent of the interpolation clock rate;
following transmission of the time delay, monitoring with the electronic triggering device an end time of the time delay;
at the end time, outputting with the electronic triggering device a trigger pulse;
monitoring with the triggering device when the follow-up time elapses following output of a last trigger pulse; and
thereafter outputting an additional trigger pulse, wherein the trigger pulse and the additional trigger pulse are outputted independent of the interpolation clock rate of the control device.

9. The method of claim 8, further comprising the steps of:
during operation of the pulse emission device, transmitting from the control device in addition to the time delay a follow-up time and a pulse number,
monitoring with the triggering device when the follow-up time elapses following output of the last trigger pulse, and outputting additional trigger pulses until a number representative of additional trigger pulses outputted since the most recent transmission of the time delay, of the follow-up time and of the pulse number corresponds to the transmitted number of pulses.

10. The method of claim 9, wherein the control device determines the pulse number from the time delay, the follow-up time and the interpolation clock rate.

11. The method of claim 8, wherein the control device determines the time delay based on a time when the last trigger pulse was outputted, a time when a subsequent desired position value is outputted, a time derivative of the desired position value determined for the at least one axis and a desired local position distance, and wherein the triggering device outputs the trigger pulses with an equidistant local position distance independent of the interpolation clock rate.

12. The method of claim 11, wherein the control device takes into consideration, when determining the time delay, a delay of an actual position value of at least one additional axis with respect to the desired position value of the at least one axis.

13. The method of claim 8, wherein the internal clock rate is greater than the interpolation clock rate.

* * * * *